US009239262B2

(12) United States Patent
Rapoport et al.

(10) Patent No.: US 9,239,262 B2
(45) Date of Patent: Jan. 19, 2016

(54) METHODS AND APPARATUS FOR AUTHENTICATING ARTICLES WITH LUMINESCENT PHOSPHOR COMPOUNDS

(75) Inventors: William Ross Rapoport, Bridgewater, NJ (US); James Kane, Lawrenceville, NJ (US); Carsten Lau, Garbsen (DE)

(73) Assignee: Honeywell International Inc., Morris Plains, NJ (US)

( * ) Notice: Subject to any disclaimer, the term of this patent is extended or adjusted under 35 U.S.C. 154(b) by 666 days.

(21) Appl. No.: 13/537,414

(22) Filed: Jun. 29, 2012

(65) Prior Publication Data

US 2013/0015369 A1    Jan. 17, 2013

Related U.S. Application Data

(60) Provisional application No. 61/508,302, filed on Jul. 15, 2011.

(51) Int. Cl.
*F21V 9/16*     (2006.01)
*G01J 1/58*     (2006.01)
(Continued)

(52) U.S. Cl.
CPC .............. *G01J 3/427* (2013.01); *G01N 21/64* (2013.01); *G07D 7/122* (2013.01); *G01N 2021/6421* (2013.01)

(58) Field of Classification Search
CPC ....... G01N 2021/1746; G01J 1/18; G01J 1/58
USPC ...................... 250/459.1, 458.1, 461.1, 214 R
See application file for complete search history.

(56) References Cited

U.S. PATENT DOCUMENTS 4,526,466 A    7/1985 Sandercock
5,949,539 A    9/1999 Britton, Jr. et al.
(Continued)

FOREIGN PATENT DOCUMENTS

CN    101044536 A    9/2007
JP    10208105 A    8/1998
(Continued)

OTHER PUBLICATIONS

International Search Report mailed Nov. 23, 2012 in International Application No. PCT/US2012/046379.
(Continued)

*Primary Examiner* — David Porta
*Assistant Examiner* — Meenakshi Sahu
(74) *Attorney, Agent, or Firm* — Ingrassia Fisher & Lorenz PC

(57) ABSTRACT

Methods and apparatus for article authentication include an exciting radiation generator that exposes an area of the article to exciting radiation, and at least two radiation detectors that detect emitted radiation from the area in a first band and in a second band that does not overlap the first band. The first band corresponds with a first emission sub-band of an emitting ion, and the second band corresponds with a second emission sub-band of the same emitting ion. A processing system calculates a comparison value that represents a mathematical relationship (e.g., a ratio) between a first intensity of the emitted radiation in the first band with a second intensity of the emitted radiation in the second band, and determines whether the comparison value compares favorably with an authentication parameter. When the comparison value compares favorably with the authentication parameter, the article is identified as being authentic.

13 Claims, 6 Drawing Sheets

(51) Int. Cl.
*G01T 1/10* (2006.01)
*G21H 3/02* (2006.01)
*G21K 5/00* (2006.01)
*H01J 65/06* (2006.01)
*H01J 65/08* (2006.01)
*G01J 3/427* (2006.01)
*G01N 21/64* (2006.01)
*G07D 7/12* (2006.01)

(56) References Cited

U.S. PATENT DOCUMENTS

2004/0061048 A1* 4/2004 Vasic et al. .................. 250/271
2006/0186348 A1 8/2006 Nguyen et al.
2008/0048106 A1 2/2008 Blanchard et al.
2009/0141961 A1 6/2009 Smith et al.
2009/0224048 A1 9/2009 Hasegawa et al.
2010/0102250 A1* 4/2010 Li et al. ...................... 250/459.1

FOREIGN PATENT DOCUMENTS

JP 2006266810 A 10/2006
WO 0046742 a1 8/2000

OTHER PUBLICATIONS

European Search Report mailed Feb. 12, 2015 in European Application No. 12814320.3.

* cited by examiner

METHODS AND APPARATUS FOR AUTHENTICATING ARTICLES WITH LUMINESCENT PHOSPHOR COMPOUNDS

CROSS-REFERENCE TO RELATED APPLICATIONS

This application claims the benefit of U.S. Provisional Application Ser. No. 61/508,302, filed Jul. 15, 2011.

TECHNICAL FIELD

The present invention generally relates to radiation emitting compounds and methods and apparatus for their authentication.

BACKGROUND

A luminescent phosphor compound is a compound that is capable of emitting detectable quantities of radiation in the infrared, visible, and/or ultraviolet spectrums upon excitation of the compound by an external energy source. A typical luminescent phosphor compound includes at least a host crystal lattice, an emitting ion (e.g., of a rare earth metal), and in some cases, a "sensitizing" ion (e.g., of a transition metal or of a different rare earth metal that can absorb and transfer the energy to the emitting rare earth metal ion). The production of radiation by a phosphor compound is accomplished by absorption of incident radiation by the emitting ion(s) or by either or both the host crystal lattice and the sensitizing ion(s), energy transfer from the host crystal lattice/sensitizing ion(s) to the emitting ion(s), and radiation of the transferred energy by the emitting ion(s).

The selected components of a phosphor compound cause the compound to have particular properties, including specific wavelengths for its excitation energy ("exciting radiation"), and specific spectral position(s) for peak(s) in energy emitted by the emitting ions of the phosphor compound ("emitted radiation"). Not every ion will have emission in all host crystal lattices. There are many examples in which radiation that has the potential for emission is quenched or the energy transfer from the absorbing ions or the host crystal lattice to the emitting ions is so poor that the radiation effects are barely observable. In other host crystal lattices, the radiation effects can be very large and with quantum efficiency near unity.

For a specific phosphor compound that does produce observable emitted radiation, the spectral position(s) of the peak(s) in its emitted radiation (i.e., its "spectral signature") may be used to uniquely identify the phosphor compound from different compounds. Primarily, the spectral signature is due to the rare earth ion(s). However, spectral perturbations may be present due to the influence of the host crystal lattice on the various ions, typically through crystal field strength and splitting. This holds true for the temporal behavior of the emitted radiation, as well.

The unique spectral properties of some phosphor compounds make them well suited for use in authenticating or identifying articles of particular value or importance (e.g., banknotes, passports, biological samples, and so on). Accordingly, luminescent phosphor compounds with known spectral signatures have been incorporated into various types of articles to enhance the ability to detect forgeries or counterfeit copies of such articles, or to track and identify the articles. For example, luminescent phosphor compounds have been incorporated into various types of articles in the form of additives, coatings, and printed or otherwise applied authentication features.

An article that includes a luminescent phosphor compound may be authenticated using specially designed authentication equipment. More particularly, a manufacturer may incorporate a known phosphor compound (e.g., an "authenticating" phosphor compound) into its "authentic" articles. Authentication equipment configured to detect the authenticity of such articles would have knowledge (e.g., stored information) of the wavelengths of absorbable exciting radiation and the spectral properties of emitted radiation associated with the authenticating phosphor compound. When provided with a sample article for authentication, the authentication equipment exposes the article to exciting radiation having wavelengths that correspond with the known wavelengths of absorption features of the luminescent phosphor that lead directly or indirectly to the desired emitted radiation. The authentication equipment senses and characterizes the spectral parameters for any emitted radiation that may be produced by the article. When the spectral signal of detected emitted radiation is within the authenticating parameter range of the detection apparatus that corresponds with the authenticating phosphor compound (referred to as the "detection parameter space"), the article may be considered authentic. Conversely, when the authentication equipment fails to sense signals expected within the detection parameter space, the article may be considered unauthentic (e.g., a forged or counterfeited article).

The above-described techniques are highly-effective at detecting and thwarting relatively unsophisticated forgery and counterfeiting activities. However, individuals with the appropriate resources and equipment may be able to employ spectrometry techniques in order to determine the components of some phosphor compounds. The phosphor compounds may then be reproduced and applied to unauthentic articles, thus compromising the authentication benefits that may otherwise be provided by a particular phosphor compound. Accordingly, although a number of phosphor compounds have been developed to facilitate article authentication in the above-described manner, it is desirable to develop additional compounds and techniques for authenticating articles, which may render forgery and counterfeiting activities more difficult, and/or which may prove beneficial for identifying and tracking articles of particular interest. Furthermore, other desirable features and characteristics of the present invention will become apparent from the subsequent detailed description of the invention and the appended claims, taken in conjunction with the accompanying drawings and this background of the invention.

BRIEF SUMMARY

An embodiment of a method for authenticating an article includes the steps of exposing an area of the article to exciting radiation, and detecting emitted radiation from the area of the article in a first band and in a second band that does not overlap the first band, where the first band corresponds with a first emission sub-band of an emitting ion, and the second band corresponds with a second emission sub-band of the emitting ion. The method further includes calculating a comparison value that represents a mathematical relationship between a first intensity of the emitted radiation in the first band with a second intensity of the emitted radiation in the second band, and determining whether the comparison value compares favorably with an authentication parameter. When the comparison value compares favorably with the authentication parameter, the article is identified as being authentic.

In a further embodiment, the first intensity is a first integrated intensity in the first band, and the second intensity is a second integrated intensity in the second band. In another further embodiment, the first intensity is a first absolute intensity measured at a pre-determined time after discontinuing the provision of the exciting radiation, and the second intensity is a second absolute intensity measured at the pre-determined time.

In another further embodiment, the first band and the second band correspond to emission bands of a single ion of an element selected from a group of elements consisting of chromium, manganese, cobalt, nickel, cerium, praseodymium, neodymium, samarium, europium, terbium, dysprosium, holmium, erbium, thulium, and ytterbium. In another further embodiment, the first band and the second band correspond to emission bands of a single ion after substitution into a host crystal lattice material selected from a group consisting of an oxide, a fluoride, an oxysulfide, a halide, a borate, a silicate, a gallate, a phosphate, a vanadate, an oxyhalide, an aluminate, a molybdate, a tungstate, a garnet, and a niobate. In yet another further embodiment, the first band and the second band correspond to emission bands of a single ion after substitution into a host crystal lattice material selected from a group consisting of yttrium oxysulfide, a yttrium aluminum garnet, and a gadolinium gallium garnet.

In another further embodiment, calculating the comparison value includes calculating a ratio between the first intensity and the second intensity, where the comparison value is the ratio.

An embodiment of an apparatus for authenticating an article includes an exciting radiation generator, a first emitted radiation detector, a second emitted radiation detector, and a processing system. The exciting radiation generator is configured to direct exciting radiation toward an area of the article. The first emitted radiation detector is configured to detect emitted radiation from the area of the article in a first band, where the first band corresponds with a first emission sub-band of an emitting ion. The second emitted radiation detector is configured to detect emitted radiation from the area of the article in a second band that does not overlap the first band, where the second band corresponds with a second emission sub-band of the emitting ion. The processing system is configured to calculate a comparison value that represents a mathematical relationship between a first intensity of the emitted radiation in the first band and a second intensity of the emitted radiation in the second band, to determine whether the comparison value compares favorably with an authentication parameter, and when the comparison value compares favorably with the authentication parameter, to identify the article as being authentic.

In a further embodiment, the processing system is configured to calculate the comparison value by calculating a ratio between the first intensity and the second intensity, where the comparison value is the ratio.

In another further embodiment, the apparatus also includes an optical element configured to separate the emitted radiation into a first beam that includes light within the first band and a second beam that includes light within the second band, where the first beam is directed toward the first radiation detector, and the second beam is directed toward the second radiation detector.

BRIEF DESCRIPTION OF THE DRAWINGS

Embodiments of the present invention will hereinafter be described in conjunction with the following figures, wherein like numerals denote like elements, and wherein.

DETAILED DESCRIPTION

Figure 1:
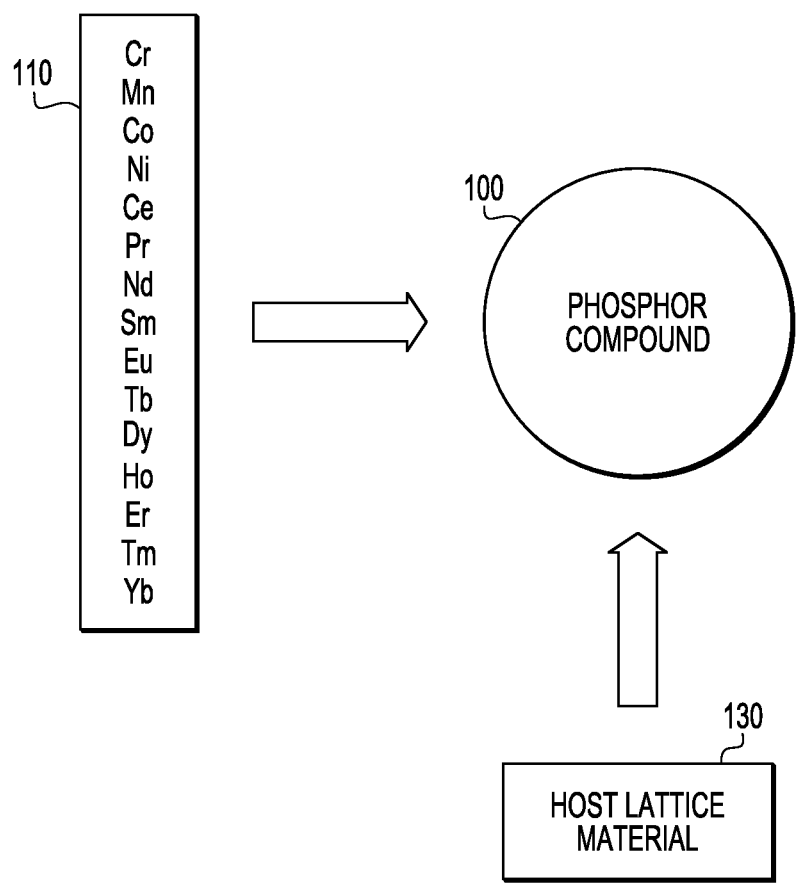
FIG. 1 depicts potential components of a phosphor compound, according to various example embodiments.

The following detailed description of various embodiments of the invention is merely exemplary in nature and is not intended to limit the inventive subject matter or the application and uses of the inventive subject matter. Furthermore, there is no intention to be bound by any theory presented in the preceding background or the following detailed description.

Luminescent phosphor compounds, articles incorporating such compounds, and methods of their manufacture and authentication are described herein. The below-described phosphor compounds may be used for a variety of applications including, but not limited to, incorporating such phosphor compounds into articles to enhance article authentication efforts. Embodiments of phosphor compounds, described below, each include at least one emitting ion and optionally one or more sensitizing ions substituted into a host crystal lattice. When one of these phosphor compounds is exposed to exciting radiation, the exciting radiation may be absorbed directly by the emitting ions, and/or optionally by one or more sensitizing ions and/or by the host crystal lattice with a subsequent transfer of the energy to the emitting ions. In whichever manner the exciting radiation is absorbed, the emitting ions of the phosphor compound produce emitted radiation having unique characteristics (e.g., a unique spectral signature and a measurable decay time constant).

After being subjected to exciting radiation, many phosphor compounds emit detectable radiation at a plurality of wavelengths within the visible and/or ultraviolet portions of the electromagnetic spectrum. Concentrated emissions within sub-bands of the electromagnetic spectrum are sometimes referred to as "emission lines," where a "sub-band" is defined herein to mean a continuous range of wavelengths within the emission spectrum of the phosphor compound within which concentrated emissions occur. For example, erbium ions emit radiation in sub-bands centered at multiple wavelengths, including relatively strong emissions at 980 nanometers (nm) and 1550 nm. According to various embodiments, methods and apparatus for authenticating an article that may include such a phosphor compound include exposing an area of the article to exciting radiation and detecting emitted radiation from the area of the article. More particularly, upon exposing the area of the article to the exciting radiation, emitted radiation emanating from the area of the article is collected and directed onto the active area(s) of one or more photodetectors (referred to also as "detectors" herein). At each detector, the impinging emitted radiation may span the entire spectral band or may span one or more sub-bands (e.g., having passed through one or more filters prior to detection). Each detector produces an electronic signal that is proportional to the intensity of the collected radiation that impinges on the active area of the detector. This intensity is referred to herein as the "integrated intensity." According to an embodiment, the authentication equipment attempts to detect an integrated intensity in multiple, non-overlapping spectral bands, where the bands correspond to known emission bands of the emitting ion within the phosphor compound. A comparison value is then calculated, which represents a mathematical relationship between the integrated intensities of the emitted radiation in the multiple bands. In an embodiment, the mathematical relationship quantifies the relative intensities of the integrated emitted radiation in the multiple bands at a predetermined time after the excitation has ceased. When the comparison value compares favorably with an authentication parameter, the article is identified as being authentic. Otherwise, the article is identified as being unauthentic.

As will be described in more detail below, a particular embodiment includes detecting emitted radiation in two, non-overlapping bands, where the comparison value is calculated based on two integrated intensity measurements corresponding to the two bands. In other embodiments, emitted radiation could be detected in more than two, non-overlapping bands, and the comparison value could be calculated based on more than two integrated intensity measurements. In addition, in a particular embodiment, the comparison value represents a mathematical ratio of an integrated first intensity corresponding to a first band and an integrated second intensity corresponding to a second band. In other embodiments, the comparison value may be based on a mathematical relationship other than a ratio. Finally, although an embodiment is described below in which an authentication method and apparatus are used to detect a phosphor compound that includes erbium-doped yttrium oxysulfide, the example phosphor compound is not intended to limit application of the various embodiments only to that compound, and the various embodiments may be used to detect emitted radiation and to perform article authentication for a wide variety of host lattices and emitting ions.

As indicated above, and according to an embodiment, the relative integrated intensities of emitted radiation in multiple bands (e.g., analysis of the ratios of the integrated intensities of emitted radiation in multiple bands) may be analyzed as a basis for authenticating an article. Analysis using the relative integrated intensities may be more desirable than an absolute integrated intensity evaluation in a single band, because various factors, which may not be readily accountable for, may affect the accuracy of an absolute integrated intensity reading. For example, the intensity of emitted radiation may be affected by soil and/or wear on the article or authentication feature, variations in the printing of authentication features, optical geometry, reflectivity of the substrate, light scattering within the substrate, size and shape of the article, substrate thickness versus penetration depth of the exciting radiation, and the power level of the laser, to name a few factors. Accordingly, in an embodiment, the mathematical relationship selected to calculate the comparison value is a mathematical relationship that is largely independent of the integrated intensity value in any single band. For example, when the mathematical relationship is a ratio between the integrated intensity values in the multiple bands, the value of the ratio is far more robust as an indicator of authenticity than the absolute value of either integrated value.

The embodiments of phosphor compounds and methods and apparatus for their detection described below increase the diversity of available materials that may be used for authentication. The mathematical relationships between emission intensities in the multiple bands that characterize the phosphor compound embodiments discussed herein may be used, in addition to decay time constants, as a measurable quantity for the purpose of authentication.

FIG. 1 depicts potential components of a phosphor compound 100, according to various example embodiments. According to various embodiments, phosphor compound 100 includes a host crystal lattice material 130 and an emitting ion 110 (i.e., a substituted emitting ion). In an alternate embodiment, phosphor compound 100 may include more than one emitting ion 110. Phosphor compound 100 also may include other materials (e.g., one or more sensitizing ions), as well, although such other materials are not specifically discussed herein.

According to an embodiment, the emitting ion 110 within phosphor compound 100 is characterized by detectable emissions at multiple different wavelengths. Preferably, the wavelengths are sufficiently separated so that different types or classes of photodetectors are used to measure the emission properties of the phosphor compound 100, although embodiments are contemplated in which the same type or class of photodetector may be used to measure emissions within different bands. According to an embodiment, phosphor compound 100 includes a single host crystal lattice material 130 and a single, rare earth emitting ion 110 that emits in multiple bands that are relatively far apart, spectrally (e.g., at least 300 nm apart). In addition, the emitting ion 110 is characterized by an emission having a branching ratio (i.e., a ratio between emission intensities in different bands) that is a strong function of the dopant percentage, in an embodiment.

As mentioned above, there are at least three mechanisms for an emitting ion 110 to receive energy for subsequent radiation. For example, in an embodiment, the emitting ion 110 may be capable of directly absorbing exciting radiation, and the emitting ion 110 may thereafter radiate at least some of the absorbed energy (typically at a different and longer wavelength from the exciting radiation). In other embodiments, the host crystal lattice material 130 or an ion thereof (e.g., a vanadate ion) may be capable of absorbing exciting radiation directly, and transferring energy to the emitting ion 110. In yet another embodiment, the host crystal lattice material 130 may contain one or more "lattice ions" that may be substituted by emitting ions 110, and optionally one or more sensitizing ions that may absorb exciting radiation and transfer the resulting energy to the emitting ions 110. Host crystal lattice absorption may be useful, in some cases, although host crystal lattice absorption is not particularly useful in a majority of cases. More typically, a transition metal ion (e.g., chromium) or a rare earth metal ion (e.g., erbium) is used as a sensitizing ion. These elements also may act as emitting ions, or they also may transfer the energy to other ions (e.g., emitting ions 110), which then radiate the transferred energy. Virtually all host crystal lattice materials may act as absorbers in the ultraviolet range because the exciting photon energy is very high in this range. However, this phenomenon may not yield any emission at all from incorporated desired ions.

The lattice ions that may be replaced are ions within the host crystal lattice material 130 that may be substituted by one or more sensitizing ions, if included, and one or more emitting ions 110, up to and including 100% substitution. 100% substitution is rare since most emitting ions are concentration quenched well below a 100% substitution level. However, there are a few notable exceptions in which particular ions and host lattice combinations that allow for greater substitutions since the physical separation of the emitting ions in the host lattice is sufficiently far apart so that the interaction term is significantly reduced.

As will be explained in more detail later, a value indicating the concentration of emitting ions 110 in the phosphor compound 100 may be determined using various embodiments. When that value corresponds with the concentration of emitting ions 110 in an authentic phosphor, an article to which the phosphor is applied may be determined to be authentic. The emitting ions 110 may be substituted at very low substitution percentages (e.g., doped at less than 1%), medium substitution percentages (e.g., from 1% to 20%), or high substitution percentages (e.g., from 20% to 100%). For example, neodymium (Nd) may be substituted at relatively low percentages up to 1.5%, holmium (Ho) and ytterbium (Yb) may be substituted at medium percentages up to 20%, and erbium (Er) may be substituted at relatively high percentages up to 60%, although these and other ions may be substituted at different percentages, as well. As used herein, the term "substituted" means substituted at any percentage, including low, medium, and high substitution percentages. The amount of each ion substituted into a host lattice material is generally described in terms of atomic percent, where the number of ions of the host lattice material that may be replaced by sensitizing and/or emitting ions is equal to 100%. An ion of a host material that allows for replacement with sensitizing and/or emitting ions may typically have similar size, similar loading, and similar coordination preference as the ions it will be replaced with. As various positions within a host crystal lattice may occur, the ions on each of these positions will be accounted for 100 atomic percent.

The host crystal lattice material 130 comprises a material into which emitting ions 110 and optionally sensitizing agents are incorporated (e.g., substituted). More particularly, the host crystal lattice material 130 may be in the form of a crystal lattice into which different chemical constituents may substitute at various positions within the lattice. The host crystal lattice material 130 should be selected to ensure that the emitting ion 110 will produce observable emissions within multiple bands, where the emissions are suitable for analysis using embodiments of authentication equipment and methods described in detail below. In various embodiments, the host crystal lattice material 130 includes a material selected from a group consisting of an oxide, a fluoride, an oxysulfide, a halide, a borate, a silicate, a gallate, a phosphate, a vanadate, an oxyhalide, an aluminate, a molybdate, a tungstate, a garnet, and a niobate, although other host crystal lattice materials may be used, as well. For example, the host crystal lattice 130 may include yttrium (Y) oxysulfide ($Y_2O_2S$ or YOS), a yttrium aluminum garnet (YAG), a gadolinium (Gd) gallium garnet, or other materials.

The emitting ion 110 includes an ion that has multiple, relatively strong emissions within sub-bands that are relatively far apart, in an embodiment. According to various embodiments, the emitting ion 110 includes an ion of an element selected from a group consisting of chromium (Cr), manganese (Mn), cobalt (Co), nickel (Ni), cerium (Ce), praseodymium (Pr), neodymium (Nd), samarium (Sm), europium (Eu), terbium (Tb), dysprosium (Dy), holmium (Ho), erbium (Er), thulium (Tm), and ytterbium (Yb). For example, the emitting ion 110 may have +3 valences, in an embodiment, although the emitting ion 110 may have different valences (e.g., +2 and/or +4), in other embodiments.

In various embodiments, the total concentration of emitting ions 110 substituted into the host crystal lattice material 130 is sufficient to cause the phosphor compound to produce a detectable emission after being appropriately subjected to exciting radiation. For example, the total concentration of emitting ions 110 substituted in the host crystal lattice material may be in a range from about 0.095 atomic percent to about 99.995 atomic percent. However, the concentration of emitting ions 110 that may be substituted while still producing the functionality of the phosphor compound (e.g., the functionality of producing an emission upon exposure to exciting radiation) depends on the type of ion that is being substituted. In other words, some ions may be substituted at relatively high percentages while still maintaining the functionality of the phosphor compound, but the functionality may be defeated if other ions are substituted at the same, relatively high percentages.

The concentration of emitting ions 110 substituted into the host crystal lattice material 130 should be greater than any background impurity level for the raw materials, while being at a sufficient concentration to achieve a desired mathematical relationship between emission intensities in multiple bands. In general, the level of rare earth impurities would not exceed a few parts per million (ppm) in a phosphor compound. Although this relatively low level of impurities may produce minor changes to emitted radiation properties of the phosphor compound, the impurities should not produce any significant changes in the properties of the phosphor compound.

According to an embodiment, an emitting ion 110 is selected that is characterized by a branching ratio that varies based on the concentration of the emitting ion 110 in the phosphor compound 100. In other words, when the host crystal lattice material 130 is doped with the emitting ion 110 at a first concentration, the phosphor compound 100 will be characterized by a first branching ratio. When the host crystal lattice material 130 is doped with the emitting ion 110 at a second, different concentration, the phosphor compound 100 will be characterized by a second, different branching ratio.

After exposure to exciting radiation, the emitting ions 110 within the phosphor compound 100 emit photons, and the integrated intensities of the emissions within multiple bands may be observed. As will be described in more detail below, a comparison value that represents a measured relationship between the integrated intensities within the multiple bands is calculated, in an embodiment, and the comparison value is compared with known parameters (e.g., an expected ratio) to determine whether the comparison value indicates that the phosphor compound 100 is an authentic compound. Accordingly, the mathematical relationship between the integrated emission intensities in the multiple bands may be used as an authentication parameter. The decay time constant also may be used as an authentication parameter, in an embodiment.

In some cases, an emitting ion (e.g., one of emitting ions 110, FIG. 1) is excited via a direct absorption process, which includes providing exciting radiation within the absorption band for the emitting ion. Alternatively, the host crystal lattice or a sensitizing ion may function as a path to excite the emitting ion, as described previously. In the former case, the emission from the emitting ion decays rapidly from the absorption resonance level to a storage level. Generally, the absorption band is above the storage level, although this is not always the case, and the decay time from the absorption resonance level is very rapid compared to the decay time from the storage level. From the storage level, spontaneous photon emission may occur at a wavelength band determined by the storage level and a lower energy level. As will be explained in more detail below, the characteristics of the emitted electromagnetic radiation from the emitting ions 110 may be used to determine whether or not the phosphor compound 100 corresponds to an "authenticating" phosphor compound.

FIGS. 2-6 depict various characteristics of phosphor compounds that include a particular crystal lattice material (i.e., YOS) doped with a particular emitting ion (i.e., erbium). It is to be understood that the below example is not to be construed as limiting, and that embodiments may be used to characterize a wide variety of other phosphor compounds. In addition, although the example phosphor compounds include compounds that are doped at particular percentages (i.e., 2.0, 4.0, 8.0. 16.0, and 32.0 atomic percent), it is to be understood that embodiments may be used to characterize phosphor compounds having different doping percentages, as well. FIGS. 2-6 are included for the purpose of illustrating the concept that the branching ratio of a phosphor compound may depend on the concentration of emitting ions substituted into the crystal host lattice material.

Figure 2:
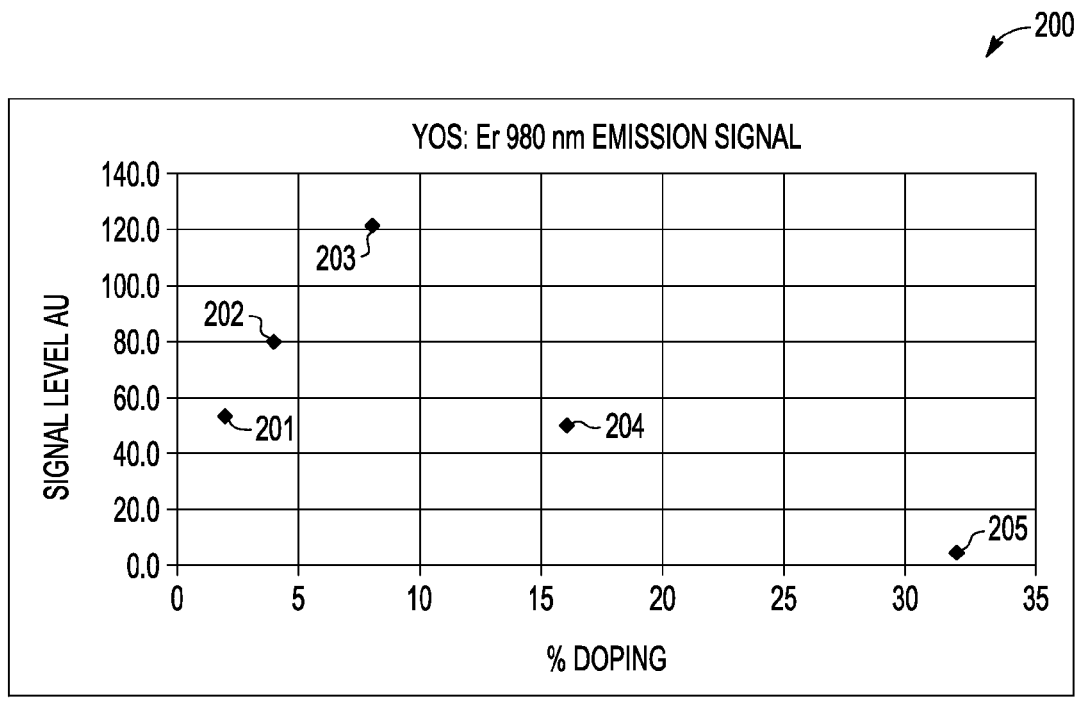
FIG. 2 is a graph illustrating emission intensities at a first wavelength as a function of doping percentage for various example phosphor compounds, according to an embodiment.

FIG. 2 is a graph 200 illustrating emission intensities (at a first wavelength) as a function of doping percentage for various example phosphor compounds, according to an embodiment. More particularly, graph 200 plots emission signal levels (in arbitrary units (AU)) at 980 nm for erbium (Er) doped YOS at various doping percentages. Point 201 corresponds to the emission signal level of a phosphor compound that includes a YOS host doped with about 2.0 atomic percent erbium, point 202 corresponds to the emission signal level of a phosphor compound that includes a YOS host doped with about 4.0 atomic percent erbium, point 203 corresponds to the emission signal level of a phosphor compound that includes a YOS host doped with about 8.0 atomic percent erbium, point 204 corresponds to the emission signal level of a phosphor compound that includes a YOS host doped with about 16.0 atomic percent erbium, and point 205 corresponds to the emission signal level of a phosphor compound that includes a YOS host doped with about 32.0 atomic percent erbium. As graph 200 indicates, the emission levels rise rapidly (from about 35.0 AU to about 120.0 AU) from 2.0 to 8.0 atomic percent doping, and then fall relatively slowly (to about 5.0 AU) from 8.0 to 32.0 atomic percent doping. Actual comparisons are normally done by integrating the intensity signal over some desired wavelength range so that a single number can be obtained that is related to the spectra. The wavelength range generally covers the emission band and little else to minimize any other contaminating signal that might affect the result.

Figure 3:
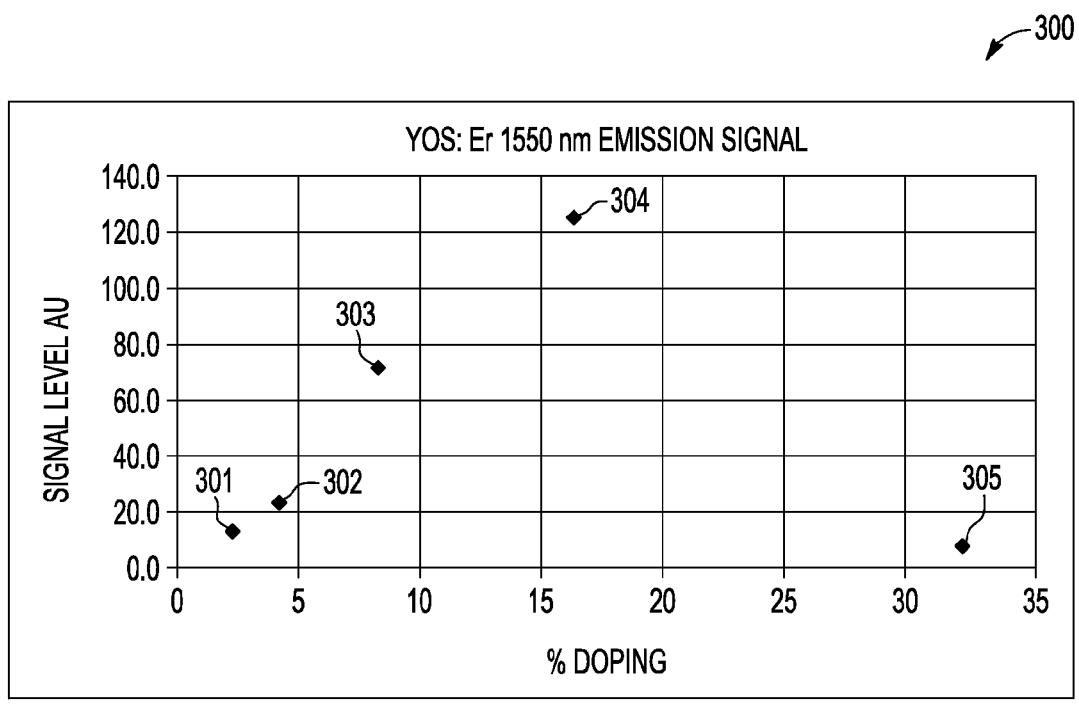
FIG. 3 is a graph illustrating emission intensities at a second wavelength as a function of doping percentage for the example phosphor compounds of FIG. 2, according to an embodiment.

FIG. 3 is a graph 300 illustrating emission intensities (at a second wavelength) as a function of doping percentage for the example phosphor compounds of FIG. 2, according to an embodiment. More particularly, graph 300 plots emission signal levels at 1550 nm for erbium doped YOS at various doping percentages. Point 301 corresponds to the emission signal level of a phosphor compound that includes a YOS host doped with about 2.0 atomic percent erbium, point 302 corresponds to the emission signal level of a phosphor compound that includes a YOS host doped with about 4.0 atomic percent erbium, point 303 corresponds to the emission signal level of a phosphor compound that includes a YOS host doped with about 8.0 atomic percent erbium, point 304 corresponds to the emission signal level of a phosphor compound that includes a YOS host doped with about 16.0 atomic percent erbium, and point 305 corresponds to the emission signal level of a phosphor compound that includes a YOS host doped with about 32.0 atomic percent erbium. As graph 300 indicates, the emission levels rise rapidly (from about 18.0 AU to about 125.0 AU) from 2.0 to 16.0 atomic percent doping, and then fall relatively rapidly (to about 5.0 AU) from 16.0 to 32.0 atomic percent doping.

Analysis of graphs 200, 300 indicates that the relationship between emission intensity and doping percentage is different for erbium doped YOS at different wavelengths. For example, at 980 nm, the emission intensity appears to peak at a doping of about 8.0 atomic percent (point 203), whereas at 1550 nm, the emission intensity appears to peak at a doping of about 16.0 atomic percent doping (point 304). Because the relationship between emission intensity and doping at various wavelengths is non-linear, the branching ratio between emission intensities varies with doping percentages.

Figure 4:
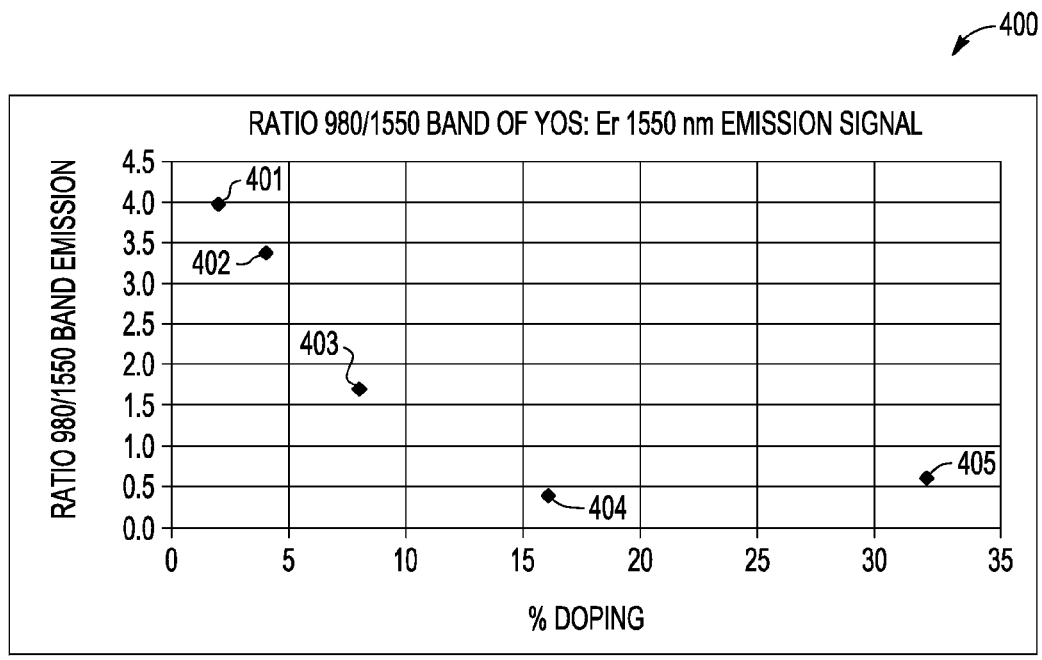
FIG. 4 is a graph illustrating ratios between emissions intensities at the first and second wavelengths as a function of doping percentage for the example phosphor compounds of FIG. 2, according to an embodiment.

FIG. 4 is a graph 400 illustrating ratios between emissions intensities at the first and second wavelengths as a function of doping percentage for the example phosphor compounds of FIG. 2, according to an embodiment. More particularly, graph 400 plots the ratio of emission intensities at 980 nm to emission intensities at 1550 nm for various doping percentages. Point 401 corresponds to the ratio of emission intensities for a phosphor compound that includes a YOS host doped with about 2.0 atomic percent erbium, point 402 corresponds to the ratio of emission intensities for a phosphor compound that includes a YOS host doped with about 4.0 atomic percent erbium, point 403 corresponds to the ratio of emission intensities for a phosphor compound that includes a YOS host doped with about 8.0 atomic percent erbium, point 404 corresponds to the ratio of emission intensities for a phosphor compound that includes a YOS host doped with about 16.0 atomic percent erbium, and point 405 corresponds to the ratio of emission intensities for a phosphor compound that includes a YOS host doped with about 32.0 atomic percent erbium. As graph 400 indicates, the ratio between integrated emission intensities at relatively low doping percentages is relatively high (i.e., about 4.0 at a doping percentage of 2.0 atomic percent), and the ratio decreases steadily to a relatively low value as the doping percentage increases (i.e., to about 0.5 at doping percentages of 16.0 atomic percent and above). As will be described in more detail below, because the ratio between integrated emission intensities in different bands varies with doping percentage, calculation of the ratio (or another mathematical relationship between the emission intensities) may be used to indicate whether a particular phosphor compound has a specific doping concentration, and thus whether the particular phosphor compound is authentic. It is desirable to make the measurements in the different bands at the same time after the excitation source is removed, since the emissions in the different bands may exhibit significantly different decay constants. In this case, the integrated emission intensity values will also change as a function of time.

Although a phosphor compound may be described as having emissions at discrete wavelengths (e.g., 980 or 1550 nm), in actuality emissions associated with a particular wavelength actually are spread across a range of wavelengths (i.e., a sub-band of the entire spectrum) with the particular wavelength roughly at the center of the band. Accordingly, in order to generate an emission intensity value, emission signals are integrated over a specified wavelength range. In measurements, this is generally done using a bandpass filter to accept a reduced wavelength range and a detector element whose response is generally somewhat flat over the wavelength range of interest. As it may be difficult to compare peak emission values, integrated emission values may be relatively simple to measure. As long as the measurement apparatus is held constant, then the ratio of integrated intensities should be stable for a given ion substitution amount. Accordingly, references to the "emission intensity" or "intensity" at a given wavelength that may be made herein actually correspond to an integrated intensity measurement across a band. This concept is represented more clearly with reference to FIGS. 5 and 6.

Figure 5:
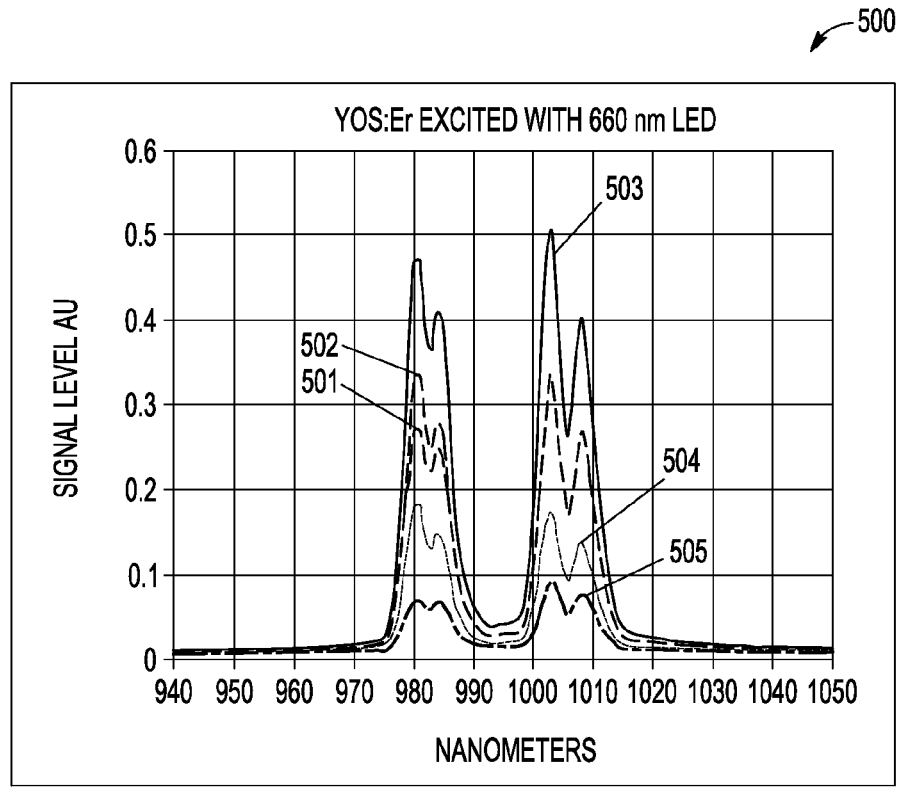
FIG. 5 is a graph illustrating emission intensities as a function of wavelength within a first band for the example phosphor compounds of FIG. 2, according to an embodiment.

FIG. 5 is a graph 500 illustrating emission intensities as a function of wavelength within a first band (i.e., a band centered at about 980 nm) for the example phosphor compounds of FIG. 2, according to an embodiment. As graph 500 indicates, significant emissions within the first band are present across a range of wavelengths (e.g., between about 975 nm and 1015 nm). Trace 501 indicates the signal level for a phosphor compound that includes a YOS host doped with about 2.0 atomic percent erbium, trace 502 indicates the signal level for a phosphor compound that includes a YOS host doped with about 4.0 atomic percent erbium, trace 503 indicates the signal level for a phosphor compound that includes a YOS host doped with about 8.0 atomic percent erbium, trace 504 indicates the signal level for a phosphor compound that includes a YOS host doped with about 16.0 atomic percent erbium, and trace 505 indicates the signal level for a phosphor compound that includes a YOS host doped with about 32.0 atomic percent erbium.

Figure 6:
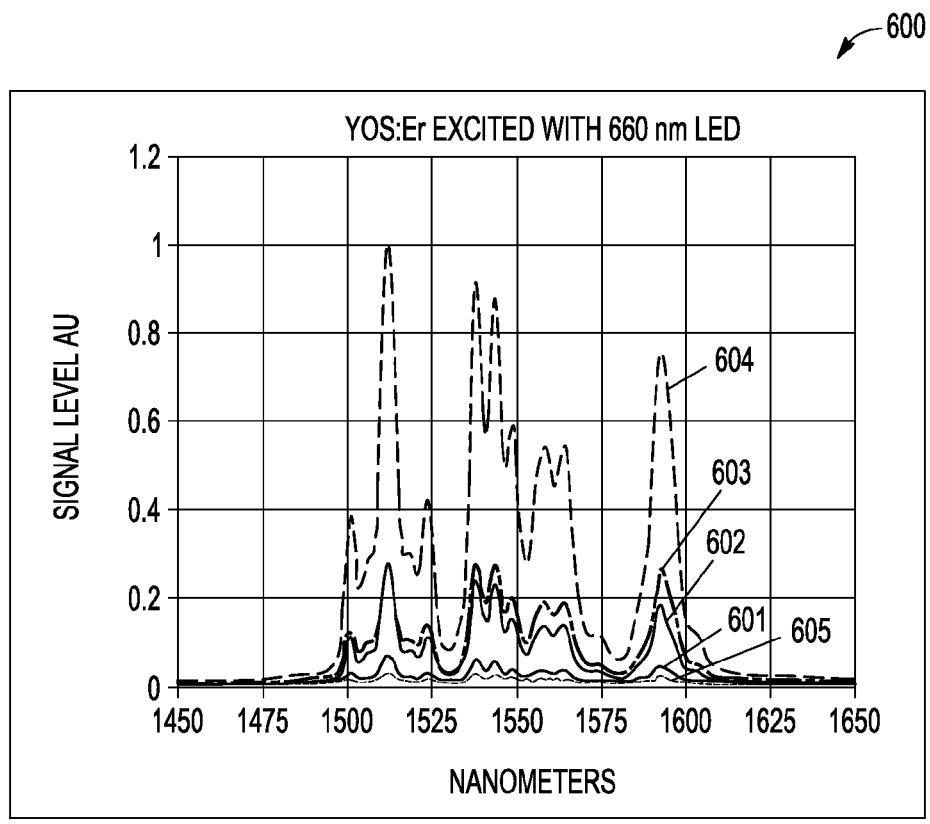
FIG. 6 is a graph illustrating emission intensities as a function of wavelength within a second band for the example phosphor compounds of FIG. 2, according to an embodiment.

FIG. 6 is a graph 600 illustrating emission intensities as a function of wavelength within a second band (i.e., a band centered at about 1550 nm) for the example phosphor compounds of FIG. 2, according to an embodiment. As graph 600 indicates, significant emissions within the first band are present across a range of wavelengths (e.g., between about 1500 nm and 1610 nm). Trace 601 indicates the signal level for a phosphor compound that includes a YOS host doped with about 2.0 atomic percent erbium, trace 602 indicates the signal level for a phosphor compound that includes a YOS host doped with about 4.0 atomic percent erbium, trace 603 indicates the signal level for a phosphor compound that includes a YOS host doped with about 8.0 atomic percent erbium, trace 604 indicates the signal level for a phosphor compound that includes a YOS host doped with about 16.0 atomic percent erbium, and trace 605 indicates the signal level for a phosphor compound that includes a YOS host doped with about 32.0 atomic percent erbium.

Figure 7:
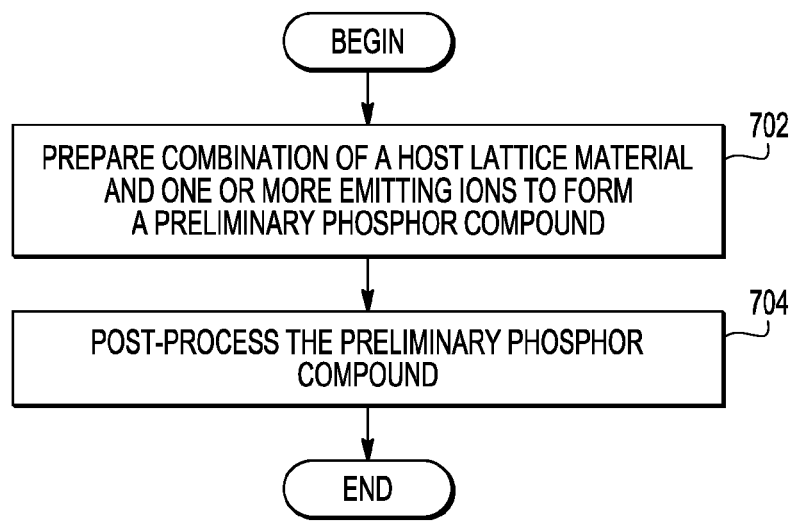
FIG. 7 is a flowchart of a method for producing a phosphor compound, in accordance with an example embodiment.

FIG. 7 is a flowchart of a method for producing a phosphor compound (e.g., phosphor compound 100, FIG. 1), in accordance with an example embodiment. Generally, a phosphor compound in accordance with an embodiment may be created using any of a number of conventional processes that are known to those of skill in the art. Creation of a phosphor compound, according to an embodiment, includes preparing a combination of a phosphor host crystal lattice material (e.g., host crystal lattice material 130, FIG. 1) and an emitting ion (e.g., one or more of emitting ions 110, FIG. 1) to form a preliminary phosphor compound in block 702. In some cases, this may be achieved using solid state chemistry. For example, when the phosphor compound is an oxide phosphor, this may include combining correct proportions of various oxides with oxides of the emitting ion. These oxides are mixed and fired for a prescribed time. In other cases, solution chemistry techniques may be used, in which the various materials are dissolved, subsequently precipitated, and subsequently fired.

Depending on the particular process used to create the compound, other materials may be included in the combination of the host crystal lattice material and the emitting ions in forming the preliminary phosphor compound. For example, various fluxing agents and other pre-cursors may be included within the preliminary phosphor compound.

In block 704, the preliminary phosphor compound is post-processed, resulting in the luminescent phosphor compound. For example, post-processing may include performing any one or more of the following processes to the preliminary phosphor compound: firing; annealing; suspension; precursor removal (e.g., to remove fluxing agents); milling; sedimentation; and sonication. The resulting phosphor compound may then be incorporated into any of a variety of articles so that the benefits of its various characteristics may be realized. For example, the phosphor compound may be incorporated into an article to provide a way of authenticating the article.

Figure 8:
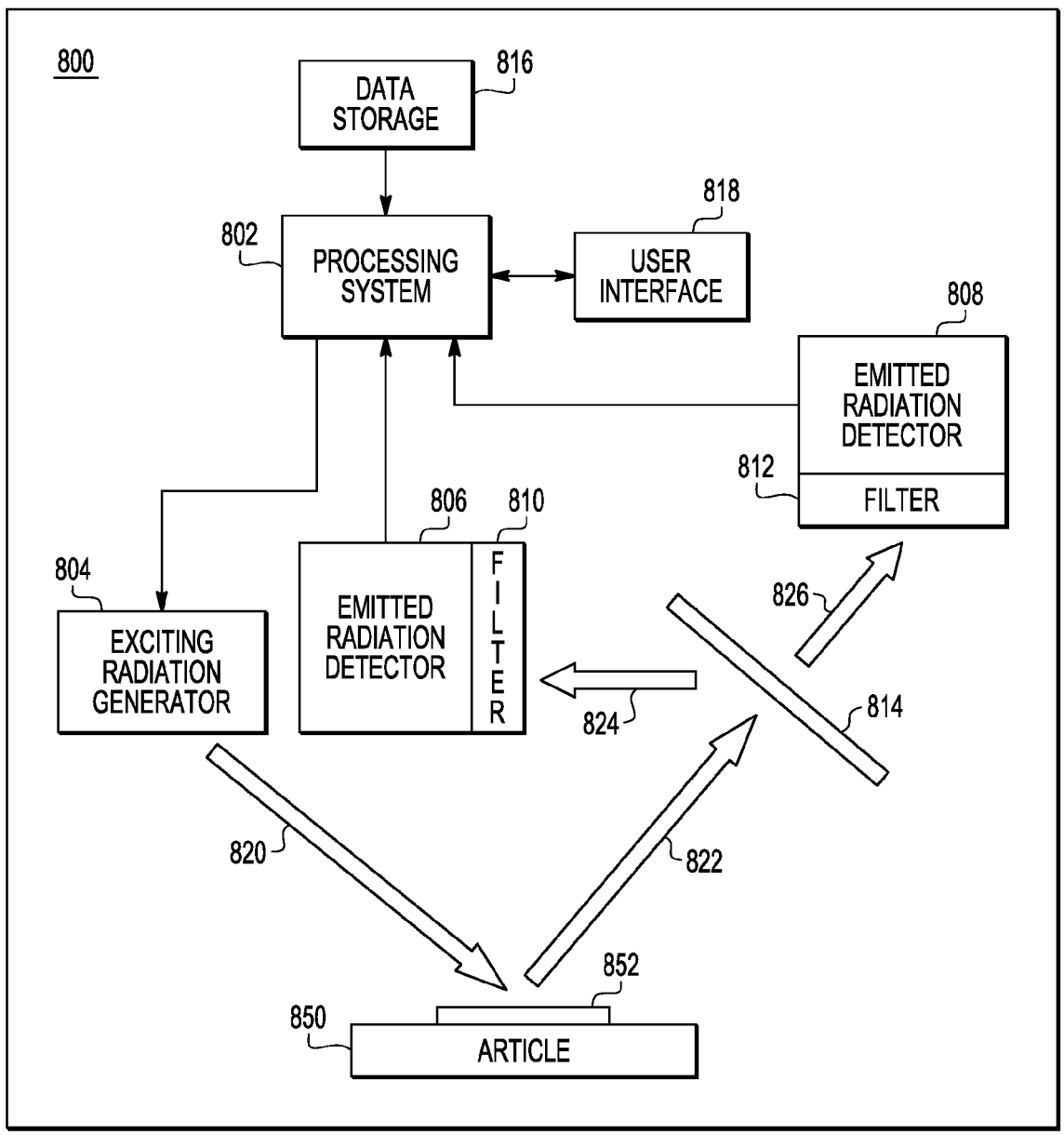
FIG. 8 is a system for authenticating an article, in accordance with an example embodiment.

FIG. 8 is a system 800 for authenticating an article 850, in accordance with an example embodiment. System 800 includes a processing system 802, an exciting radiation generator 804, multiple emitted radiation photodetectors ("detectors") 806, 808 with associated optical filters (filters) 810, 812, an optical element 814, data storage 816, and a user interface 818, according to an embodiment. Processing system 802 may include one or more processors and associated circuitry, which is configured to implement control and analysis processes (e.g., in the form of executable software algorithms) associated with authenticating an article (e.g., article 850).

According to an embodiment, processing system 802 is configured to provide control signals to exciting radiation generator 804, which cause exciting radiation generator 804 to direct exciting radiation 820 toward an area 852 of article 850 (e.g., an area in or on which an authentication feature that includes a phosphor compound should be located). Desirably, area 852 corresponds to an area which, for an authentic article, includes an authentication feature that is likely to have a consistently produced and concentrated authentic phosphor material (e.g., an area that is relatively robust to process variation). In the control signals, processing system 802 may specify the timing (e.g., start time, stop time, and/or duration) of the provision of exciting radiation, and/or other parameters associated with the particular exciting radiation to be generated (e.g., intensities and/or other parameters). Typically, the bandwidth of the exciting radiation is pre-determined based on the excitation source that is included as part of the exciting radiation generator 804 (e.g., the bandwidth of excitation produced by a selected light emitting diode or laser diode). The various timing and/or radiation generation parameters may be retrieved from data storage 816, for example. Exciting radiation generator 804 may include, for example, one or more lasers, laser diodes, light-emitting diodes (LEDs), incandescent filaments, lamps, or other excitation sources.

In addition to controlling exciting radiation generator 804, processing system 802 is configured to provide control inputs to emitted radiation detectors 806, 808, which cause emitted radiation detectors 806, 808 to attempt to detect emitted radiation 822, 824, 826 produced by the area 852 of article 850 in response to having absorbed (either directly or indirectly) at least some of the exciting radiation 820.

According to an embodiment, the emitted radiation 822 impinges upon the optical element 814, which separates the emitted radiation 822 into first and second beams 824, 826. The first beam 824 includes light within a first band, and the second beam 826 includes light within a second band that does not overlap and is separated from the first band. Optical element 814 directs the first beam 824 toward one of detectors 806, and directs the second beam 826 toward the other of detectors 808. According to an embodiment, optical element 814 is configured to reflect the first beam 824 and to pass the second beam 826. For example, optical element 814 may be an element selected from a group consisting of a polychromator, a prism, diffraction grating, a thin-film filter, an interference filter, a dichroic filter, a dichroic mirror, and a dichroic reflector. An advantage to such an optical element 814 is that it enables both detectors 806, 808 simultaneously to receive components of an emission that emanated from the same area 852 of the article 850, thus maximizing correlation of the resulting intensity measurements.

Each emitted radiation detector 806, 808 may include, for example, a spectral filter 810, 812, one or more electro-optical sensors, photomultiplier tubes, avalanche photodiodes, photodiodes, charge-coupled devices, charge-injection devices, photographic films, or other detection devices. In a particular embodiment, each emitted radiation detector 806, 808 includes a spectral filter 810, 812 positioned between the article 850 and a photodetector. The spectral filters 810, 812 are configured to filter the beams 824, 826 before they are provided to detectors 806, 808, so that emitted radiation only within a sub-band of the entire spectrum actually impinges upon the active area of each detector 806, 808. The spectral filters 810, 812 may include, for example, long pass, bandpass, or other types of filters configured to pass light only within a spectral band of interest, and to reject all other light. For example, if system 800 is configured to authenticate articles that may include a phosphor such as the previously-described phosphor examples (e.g., erbium doped YOS), one of the spectral filters 810, 812 may include a long pass filter (e.g., a 1500 nm long pass filter), and the other of the spectral filters 810, 812 may include a Full Width at Half Maximum (FWHM) bandpass filter (e.g., a 20 nm FWHM bandpass filter centered at 980 nm).

Each of detectors 806, 808 has sensitivity within the spectral band of interest, and accordingly may detect light passing through the spectral filter 810, 812 that is within that spectral band. According to an embodiment, one of detectors 806, 808 is configured to detect emitted radiation within a first band of interest (e.g., 980 nm or some other band), and the other of detectors 806, 808 is configured to detect emitted radiation within a second band of interest (e.g., 1550 nm or some other band). The detectors 806, 808 may be of the same type or of different types. According to a particular embodiment, the detectors 806, 808 are of different types. For example, one of detectors 806, 808 may include a silicon detector, and the other of detectors 806, 808 may include an indium-gallium-arsenide (InGaAs) detector (e.g., a telecom type or extended InGaAs). Other types of detectors that are capable of detecting emitted radiation within a band of interest may be used, in other embodiments (e.g., lead-sulfide, lead-selenide, germanium, indium-antimonide, indium-arsenide, platinum-silicide, indium-antimonide, and so on). In an alternate embodiment, a single detector may be employed, which is capable of detecting emitted radiation in all bands of interest. In such an embodiment, optical element 814 may be excluded from system 800. In other alternate embodiments, more than two detectors may be employed to detect emitted radiation in more than two bands of interest. In such embodiments, a plurality of optical elements may be employed to direct distinct beams toward the multiple detectors.

As mentioned previously, each detector 806, 808 produces an electronic signal that is proportional to the intensity of the collected radiation that impinges on the active area of the detector 806, 808. More particularly, each detector 806, 808 produces a signal (e.g., one or more digitized intensity values) representing the integrated intensity across the sub-band of emitted radiation received by the detector 806, 808. Desirably, when multiple detectors 806, 808 are used in the system (e.g., as in the system 800 of FIG. 8), the value of the integrated intensity is electronically captured by each detector 806, 808 at the same time, as simultaneous integrated intensity measurements are likely to yield a more robust and accurate comparison. Each emitted radiation detector 806, 808 may digitize intensity values at one or more pre-selected intervals (e.g., starting at t=0, and then every 0.1 milliseconds thereafter, for several intervals). In addition, each emitted radiation detector 806, 808 provides information to processing system 802 (e.g., the digitized intensity values), which enables the spectral and temporal properties of the emitted radiation 822 to be characterized.

Processing system 802 is configured to analyze such information, upon its receipt, in order to determine whether or not the temporal and spectral properties of any detected radiation corresponds to the temporal and spectral properties of an "authenticating" phosphor compound (i.e., a phosphor compound having known temporal and spectral properties, which is used for identification and/or authentication purposes).

As will be discussed in more detail below, processing system 802 is configured to calculate a comparison value that represents a mathematical relationship between a first integrated intensity of the emitted radiation in a first band and a second integrated intensity of the emitted radiation in a second band that does not overlap the first band, in an embodiment. Processing system 802 is further configured to determine whether the comparison value compares favorably with expected, pre-determined authentication parameters (e.g., stored in data storage 816), and when the comparison value compares favorably with the authentication parameters, to identify the article as being authentic. Conversely, when the comparison value does not compare favorably with the authentication parameters, processing system 802 is configured to identify the article as being unauthentic. In a particular embodiment, the comparison value is a ratio between the first integrated intensity and the second integrated intensity, and the authentication parameters include values indicating a range of ratios within which the ratio should fall for the article to be designated as being authentic. In other embodiments, the comparison value may be a value calculated based on a different mathematical relationship between the first and second integrated intensities. In still other embodiments, the comparison value may be a value calculated based on actual intensities at a defined time after the excitation source (e.g., emitted radiation 822) is removed or turned off. The combination of each optical filter 810, 812 and detector 806, 808 integrates the signal over a corresponding wavelength range. After the excitation source is removed or turned off, the intensity value then decreases due to the decay properties of the emission. As long as the measurement time remains fixed for the system 800, the ratio of intensities for an authentic material should remain relatively constant.

In addition, in an embodiment, processing system 802 may determine whether the temporal properties of the detected radiation compare favorably with other pre-defined authentication parameters. For example, processing system 802 may determine whether a decay time of the emitted radiation compares favorably with a decay time parameter. When the decay time does not compare favorably with the decay time parameter, processing system 802 may identify the article as being unauthentic.

When the temporal and spectral properties of detected radiation do correspond to the expected pre-determined authentication parameters of an authenticating phosphor compound, processing system 802 may take some action associated with identifying article 850 as an authentic article. For example, processing system 802 may send a signal to user interface 818, which causes user interface 818 to produce a user-perceptible indication of authenticity (e.g., a displayed indicia, a light, a sound, and so on), and/or processing system 802 may cause a routing component of system 800 (not illustrated) to route article 850 toward a route or bin assigned for authentic articles. Alternatively, when the temporal and/or spectral properties of the detected radiation do not correspond to the expected pre-determined authentication parameters of an authenticating phosphor compound, processing system 802 may take some action associated with identifying article 850 as an unauthentic article. For example, processing system 802 may send a signal to user interface 818, which causes user interface 818 to produce a user-perceptible indication of non-authenticity (e.g., a displayed indicia, a light, a sound, and so on), and/or processing system 802 may cause a routing component of system 800 (not illustrated) to route article 850 toward a route or bin assigned for non-authentic articles.

User interface 818 may include any of a number of components that may be manipulated by a user to provide inputs to system 800 (e.g., keyboards, buttons, touchscreens, and so on), or which may be controlled by processing system 802 to produce user-perceptible indicia (e.g., display screens, lights, speakers, and so on). The above-described process may be initiated in response to user inputs provided through the user's interaction with user interface 818, for example. Alternatively, the above-described process may be initiated automatically by the system 800, such as when the article 850 has been positioned in a location at which the excitation and detection processes may be performed.

Figure 9:
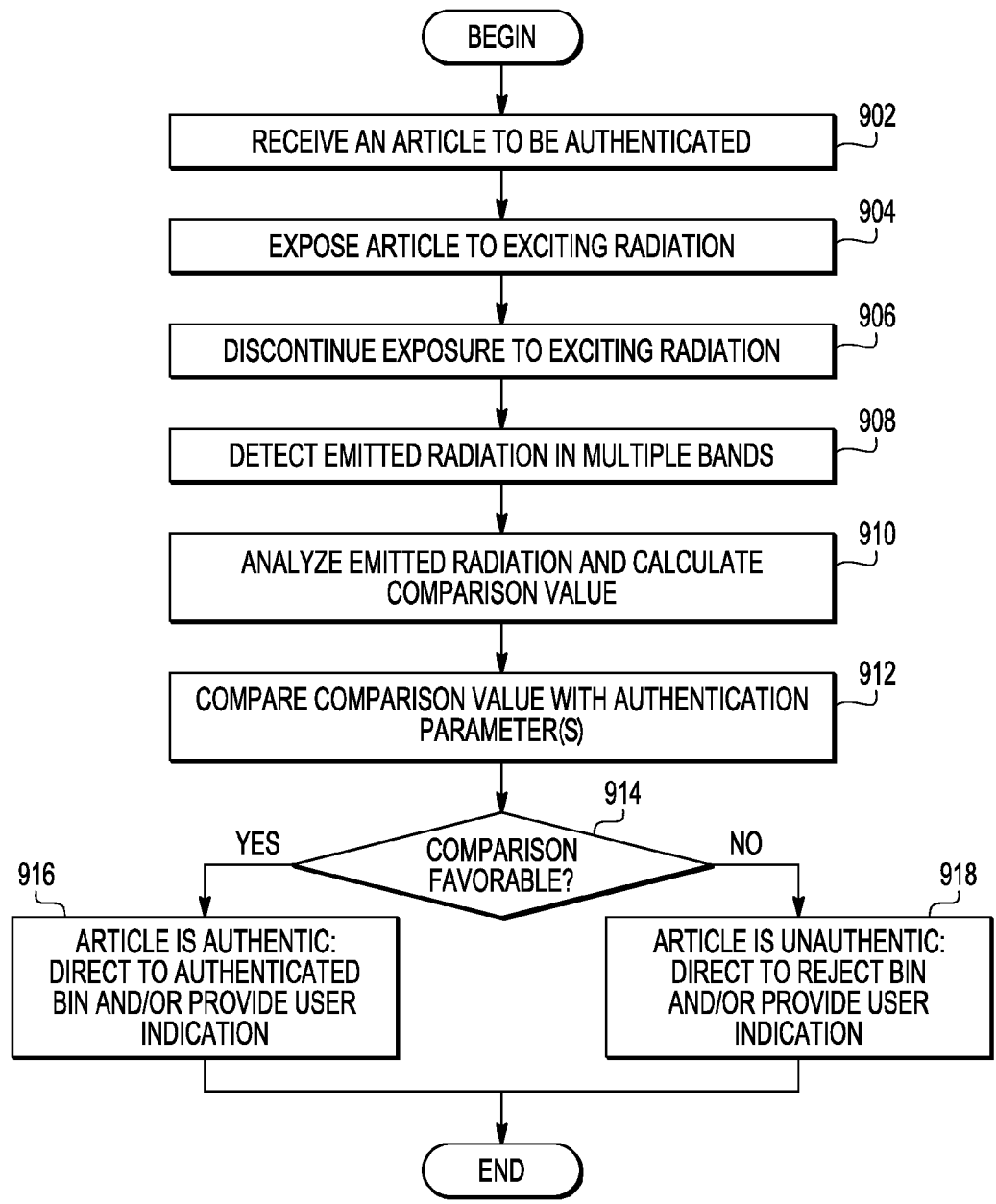
FIG. 9 is a flowchart of a method for performing authentication of an article that may include a phosphor compound, in accordance with an example embodiment.

FIG. 9 is a flowchart of a method for performing authentication of an article that may include a phosphor compound, in accordance with an example embodiment. For example, embodiments of the method depicted in FIG. 9 may be performed by an authentication system (e.g., authentication system 800, FIG. 8). The method may begin, in block 902, when an article to be authenticated (e.g., article 850, FIG. 8) is received by the authentication system. For example, the article may be manually placed within an appropriate receptacle of the authentication system, or the article may automatically be routed into the receptacle (e.g., by a sorting or conveyor system).

In block 904, the article is exposed to exciting radiation. For example, the article may be moved to an excitation position (e.g., under an excitation window), and the processing system (e.g., processing system 802, FIG. 8) may send a control signal to an exciting radiation generator (e.g., exciting radiation generator 804, FIG. 8) that causes the exciting radiation generator to direct exciting radiation toward the article. Alternatively, the exciting radiation generator may continuously provide the exciting radiation or the exciting radiation may be modulated.

In block 906, provision of the exciting radiation to the article is discontinued. This may be accomplished either by turning the exciting radiation off (e.g., in a system in which the article may remain stationary and the exciting radiation is pulsed), or by moving the article away from the area where the exciting radiation is being directed and to a detection position (e.g., under a detection window). In an alternate embodiment, provision of the exciting radiation may continue while the system performs the detection process described below.

In block 908, the authentication system detects emitted radiation within multiple bands from the article (e.g., by emitted radiation detectors 806, 808, FIG. 8). Detection may be performed at one or more detection intervals, which are measured from the time that direction of the exciting radiation toward the article was discontinued. According to an embodiment, the system is configured to detect emitted radiation in a first band and a second band, although the system may be configured to detect emitted radiation in more than two bands, as well.

In block 910, information quantizing the intensities of detected, emitted radiation within the multiple bands is analyzed (e.g., by processing system 802, FIG. 8). In an embodiment, a mathematical relationship between the intensities of emitted radiation in the multiple bands is calculated. In a particular embodiment, the mathematical relationship is a ratio, and the comparison value, C, may be calculated according to:

$$C = I_{B1}/I_{B2}, \qquad \text{(Equation 1)}$$

where $I_{B1}$ denotes the integrated emission intensity (or an absolute intensity measured at a pre-determined time after the excitation is removed) measured in a first band, and $I_{B2}$ denotes the integrated emission intensity (or an absolute intensity measured at a pre-determined time after the excitation is removed) measured in a second band.

In other embodiments, the comparison value may be determined based on multiple emitted radiation intensities detected at a plurality of times after discontinuation of the exciting radiation. For example, an average intensity may be calculated for each band, and the comparison value may be a ratio of the average intensities. Alternatively, a ratio of the intensities within the bands may be calculated for each of multiple detection times, and the comparison value may be an average of the ratios. In other embodiments, other mathematical relationships may be used, which include multiple intensity measurements as variables. The mathematical relationship selected may depend on the emission characteristics of a phosphor compound being authenticated, along with other factors. For example, for a particular phosphor compound, if emissions in one band decay very rapidly (e.g., the emission has a small time constant) when compared with emissions in another band, a ratio between the intensities may have the value characterizing the rapidly decaying emission in the numerator to avoid rapid increases in the ratio over small time increments. According to an embodiment, the gains for a detection system (e.g., system 800, FIG. 8) may be set so that a desired ratio is set to unity (or some other desired value). In such an embodiment, variations in the ratio may be relatively easy to detect, and small measurement errors may not result in large deviations.

According to an embodiment, analysis of the emitted radiation also may include determining the decay time of emitted radiation within one or more bands. In an embodiment, the decay time(s) may be determined based on the detected intensities of the emitted radiation at multiple times (e.g., t=0, t=0.1 millisecond, and so on). Upon removal of the exciting radiation, the intensity of the emission decays over time, and the rate of decay for the emitting ion can be characterized by the decay time constant. For example, for a simple exponential decay in emission intensity, the decay time constant can be represented by the constant τ in the equation:

$$I(t) = I_0 e^{-t/\tau}, \qquad \text{(Equation 2)}$$

where t denotes time, I(t) denotes the emission intensity at time t, and $I_0$ denotes the emission intensity at t=0 (e.g., t=0 may correspond to the instant when the provision of exciting radiation is discontinued). Although the emission intensity for some phosphor compounds may decay according to the above, simple exponential formula, the emission intensity for other phosphor compounds may be affected by multiple exponential decays (e.g., when multiple mechanisms affecting the decay are present). In some cases, a phosphor compound may not exhibit a simple single exponential decay, especially when energy transfer is part of the mechanism.

In block 912, the comparison value is compared with one or more authentication parameters. For example, authentication parameters may include a lower limit, an upper limit, a range, and so on. More particularly, in an embodiment in which the comparison value is a range of ratios of emission intensities in a first and second band, authentication parameters may include upper and lower limits defining a range of ratios. In such a case, a favorable comparison of the comparison value with the authentication parameters would be a comparison in which the ratio of emission intensities (the calculated comparison value from block 908) falls within the range of ratios (i.e., the ratio is larger than the lower limit and smaller than the upper limit). Conversely, an unfavorable comparison of the comparison value with the authentication parameters would be a comparison in which the ratio of emission intensities either is smaller than the lower limit or larger than the upper limit. In addition to evaluating the comparison value, a determination may be made whether the decay time is within a specified range for the particular phosphor compound.

In block 914, when a determination is made that the comparison value compares favorably with the authentication parameters (and, optionally, the decay time constant compares favorably with a range of acceptable decay times), the system may identify the article as being "authentic," and may take a corresponding action, in block 914. For example, the system may produce a user-perceptible indication of authenticity, and/or may cause a routing component of the system to route the article toward a route or bin assigned for authentic articles. Alternatively, when a determination is made that the comparison value does not compare favorably with the authentication parameters (or, optionally, the decay time constant does not compare favorably with a range of acceptable decay times), the system may identify the article as being "unauthentic," and may take a corresponding action, in block 918. For example, the system may produce a user-perceptible indication of non-authenticity, and/or may cause a routing component of the system to route the article toward a route or bin assigned for unauthentic articles.

Figure 10:
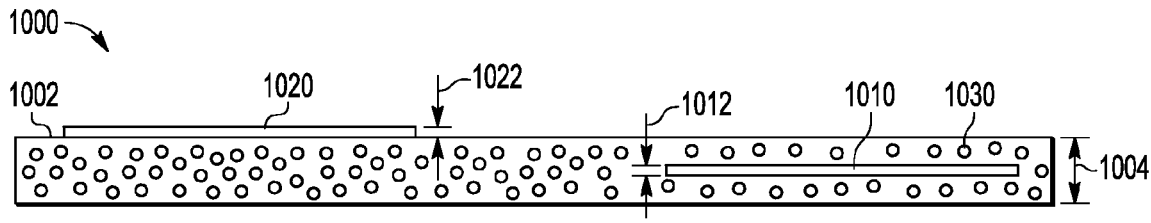
FIG. 10 depicts a cross-sectional view of an article with phosphor-containing, embedded and printed authentication features, according to an example embodiment.

FIG. 10 depicts a cross-sectional view of an article 1000 that includes a phosphor-containing material, according to an example embodiment. For example, an embodiment of an article 1000 may include embedded and/or surface-applied authentication features 1010, 1020, and/or the article 1000 may include phosphor particles 1030 that are evenly or unevenly dispersed within one or more components of the article 1000 (e.g., within substrate 1002 and/or one or more layers or other components of the article). The various relative dimensions of the authentication features 1010, 1020 and particles 1030 may not be to scale in FIG. 10. Although article 1000 is illustrated to include both embedded and surface-applied authentication features 1010, 1020 and particles 1030, another article may include one or a combination of embedded authentication features, surface-applied authentication features, and dispersed phosphor particles. Finally, although only one each of embedded authentication feature 1010, 1020 are shown in FIG. 10, an article may include more than one of either type of authentication feature 1010, 1020.

Article 1000 includes a substrate 1002, which may be rigid or flexible, and which may be formed from one or more layers or components, in various embodiments. The variety of configurations of substrate 1002 are too numerous to mention, as the phosphor compounds of the various embodiments may be used in conjunction with a vast array of different types of articles. Therefore, although a simple, unitary substrate 1002 is illustrated in FIG. 10, it is to be understood that substrate 1002 may have any of a variety of different configurations. In addition, although inanimate, solid articles are discussed herein, it is to be understood that an "article" also may include a human, an animal, a biological specimen, a liquid sample, and virtually any other object or material into or onto which a phosphor compound of an embodiment may be included.

Embedded authentication feature 1010 comprises one or more rigid or flexible materials in which or onto which a phosphor compound of an embodiment is included. For example, embedded authentication feature 1010 may be configured in the form of a discrete, rigid or flexible substrate, a security thread, or another type of structure. According to various embodiments, embedded authentication feature 1010 may have a thickness 1012 in a range of about one micron up to the thickness 1004 of the substrate 1002, and embedded authentication feature 1010 may have a width and length that is less than or equal to the width and length of the substrate 1002.

Surface-applied authentication feature 1020 may be, for example, a printed authentication feature or an authentication feature that includes one or more rigid or flexible materials into which or onto which a phosphor compound of an embodiment is included. For example, the surface-applied authentication feature 1020 may comprise an ink, pigment, coating, or paint that includes a phosphor compound as previously described. Alternatively, the surface-applied authentication feature 1020 may comprise one or more rigid or flexible materials into which or onto which a phosphor compound is included, where the substrate is then adhered or otherwise attached to a surface of the article substrate 1002. According to various embodiments, surface-applied authentication feature 1020 may have a thickness 1022 of about one micron or more, and surface-applied authentication feature 1020 may have a width and length that is less than or equal to the width and length of the substrate 1002.

Phosphor particles 1030 may be evenly or unevenly dispersed within substrate 1002, as shown in FIG. 10, or within one or more other components of the article 1000 (e.g., within one or more layers or other components of the article), in other embodiments. The phosphor particles 1030 may be dispersed within substrate 1002 or another component, for example, by mixing particles 1030 into a base material (e.g., paper pulp, plastic base resin, and so on) for the substrate 1002 or other component, and/or by impregnating the substrate 1002 or other component with a colloidal dispersion of the particles 1030. Impregnation may be performed, for example, by a printing, dripping, or spraying process. Phosphor particles 1030 may have particle sizes in a range from 1 micron to 20 microns, in an embodiment, although the phosphor particles 1030 may be smaller or larger than the above-given range, as well.

In various embodiments, article 1000 may be any type of article selected from a group that includes, but is not limited to, an identification card, a driver's license, a passport, identity papers, a banknote, a check, a document, a paper, a stock certificate, a packaging component, a credit card, a bank card, a label, a seal, a postage stamp, a liquid, a human, an animal, and a biological sample. Substrate 1002 may be any of various types of substrates, and includes one or more materials selected from a group that includes, but is not limited to, paper, a polymer, glass, a metal, a textile, and a fiber.

Various embodiments of methods and apparatus for authenticating luminescent phosphor compounds and articles with which they are incorporated have been described above. Embodiments of phosphor compounds with which the methods and apparatus may be used include a dopant (e.g., substituted emitting ion) characterized by multiple emission sub-bands. Desirably, the doping concentration may be well controlled in the phosphor growth process to produce a stable ratio between the emission sub-bands. According to an embodiment, the spectral emissions are relatively far apart so that a different type of detector can be used to detect each spectral emission of interest. Such an embodiment may facilitate the creation of relatively robust authenticating phosphor compounds, because conventional detectors may be incapable of differentiating between compounds having different emitting ion concentrations. Therefore, attempts to create the phosphor compound having confidential doping concentrations would not likely be successful. In addition, because the growth process may significantly affect the decay time constants, the growth process also may affect the ratio readings. This implies that not only do confidential dopant levels add to the robustness of the phosphor compound, but the use of growth processes other than a well-controlled and/or confidential growth process may not produce a phosphor compound that will produce the same ratio readings.

When an embodiment of a phosphor compound is contained in a carrier such as a chromophore containing ink, the absorbance of the ink also may change the ratio of the signals, and the effects of the ink may be accounted for in the authentication process. Similar effects also may occur when the phosphor compound is included in paper or other mediums.

An advantage of the various embodiments is that the production process (and the quality assurance associated with the process) may produce a phosphor compound having an emission ratio that is difficult to achieve without access to detailed information regarding the production process and the constituents of the phosphor compound. As described in detail above, the use of a single emitting ion at a pre-defined concentration results in a predictable emission intensity ratio. The process is also robust to mixing variations and particle size distributions to first order. In contrast, dual type of taggant systems are far more susceptible to errors.

In addition, the use of a single excitation source and analysis of constituents of a single emitted beam according to an embodiment provides for more robust authentication, because the energy flows through the electronic manifold in a uniform and reproducible fashion. This may substantially eliminate errors due to changing excitation levels and spectral drift of the sources. Those error terms only result in a signal magnitude change, which is removed through the signal ratio method.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the inventive subject matter in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for authenticating an article, the method comprising the steps of:
   exposing an area of the article to exciting radiation, wherein the area of the article includes a phosphor compound that emits detectable radiation at a plurality of wavelengths and wherein the phosphor compound comprises an emitting ion and a host crystal lattice material;
   detecting emitted radiation from the area of the article in a first band and in a second band that does not overlap the first band, wherein the first band corresponds with a first emission sub-band of the emitting ion within the phosphor compound, and the second band corresponds with a second emission sub-band of the emitting ion within the phosphor compound;
   calculating a comparison value that represents a mathematical relationship between a first intensity of the emitted radiation in the first band with a second intensity of the emitted radiation in the second band; and
   determining whether the comparison value compares favorably with an authentication parameter.

2. The method of claim 1, wherein the first intensity is a first integrated intensity in the first band, and the second intensity is a second integrated intensity in the second band.

3. The method of claim 1, further comprising, after the exposing step:
   discontinuing provision of the exciting radiation at a first time, wherein detecting the emitted radiation is performed after discontinuing the provision of the exciting radiation.

4. The method of claim 3, wherein the first intensity is a first absolute intensity measured at a pre-determined time after the first time, and the second intensity is a second absolute intensity measured at the pre-determined time after the first time.

5. The method of claim 1, wherein the first band and the second band correspond to emission bands of a single ion of an element selected from a group of elements consisting of chromium, manganese, cobalt, nickel, cerium, praseodymium, neodymium, samarium, europium, terbium, dysprosium, holmium, erbium, thulium, and ytterbium.

6. The method of claim 1, wherein the first band and the second band correspond to emission bands of a single ion after substitution into the host crystal lattice material, wherein the host crystal lattice material is selected from a group consisting of an oxide, a fluoride, an oxysulfide, a halide, a borate, a silicate, a gallate, a phosphate, a vanadate, an oxyhalide, an aluminate, a molybdate, a tungstate, a garnet, and a niobate.

7. The method of claim 1, wherein the first band and the second band correspond to emission bands of a single ion after substitution into the host crystal lattice material, wherein the host crystal lattice material is selected from a group consisting of yttrium oxysulfide, a yttrium aluminum garnet, and a gadolinium gallium garnet.

8. The method of claim 1, wherein detecting the emitted radiation comprises the steps of:
   separating the emitted radiation into a first beam that includes light within the first band and a second beam that includes light within the second band;
   detecting the first intensity from the first beam; and
   detecting the second intensity from the second beam.

9. The method of claim 1, wherein detecting the emitted radiation comprises the steps of:
   separating the emitted radiation into a first beam that includes light within the first band and a second beam that includes light within the second band;
   filtering the first beam with a first filter to produce a first filtered beam;
   filtering the second beam with a second filter to produce a second filtered beam;
   detecting the first intensity from the first filtered beam; and
   detecting the second intensity from the second filtered beam.

10. The method of claim 1, wherein calculating the comparison value comprises the step of:

calculating a ratio between the first intensity and the second intensity, wherein the comparison value is the ratio.

11. The method of claim 1, wherein determining whether the comparison value compares favorably with an authentication parameter comprises the steps of:
   determining whether the comparison value falls within a range defined by a lower limit and an upper limit;
   when the comparison value falls within the range, determining that the comparison value compares favorably with the authentication parameter, wherein the method further comprises identifying the article as being authentic; and
   when the comparison value falls outside the range, determining that the comparison value does not compare favorably with the authentication parameter, wherein the method further comprises identifying the article as being unauthentic.

12. The method of claim 1, further comprising the steps of:
   determining whether a decay time of the emitted radiation compares favorably with a decay time parameter; and
   when the decay time does not compare favorably with the decay time parameter, identifying the article as being unauthentic.

13. The method of claim 1, further comprising the step of:
   when the comparison value does not compare favorably with the authentication parameter, identifying the article as being unauthentic.

\* \* \* \* \*